United States Patent
Murthy et al.

Patent Number: 6,055,295
Date of Patent: Apr. 25, 2000

[54] METHOD AND APPARATUS FOR AUTOMATIC COLLIMATION IN X-RAY PERIPHERAL IMAGING

[75] Inventors: Sreerama K. Murthy, Monmouth Junction; Jianzhong Qian, Princeton Junction, both of N.J.

[73] Assignee: Siemens Corporate Research, Inc., Princeton, N.J.

[21] Appl. No.: 09/015,725

[22] Filed: Jan. 29, 1998

[51] Int. Cl.$^7$ .................................................. G21K 1/04
[52] U.S. Cl. ........................ 378/151; 378/98.7; 378/145
[58] Field of Search .................................. 378/145, 146, 378/147, 156, 151, 152, 153, 98.7

[56] References Cited

U.S. PATENT DOCUMENTS

| | | | |
|---|---|---|---|
| 4,672,652 | 6/1987 | Huttenrauch et al. | 378/152 |
| 4,817,125 | 3/1989 | Sklebitz | 378/152 |
| 5,287,396 | 2/1994 | Stegehuis | 378/98.2 |
| 5,349,625 | 9/1994 | Born et al. | 378/95 |
| 5,369,678 | 11/1994 | Chiu et al. | 378/62 |
| 5,412,704 | 5/1995 | Horbaschek | 378/98.2 |

OTHER PUBLICATIONS

"Classification and Regression Trees", Breiman et al., Chapman & Hall, 1993, pp. 20–27.

*Primary Examiner*—David P. Porta
*Attorney, Agent, or Firm*—Adel A. Ahmed

[57] ABSTRACT

A method for automatically setting a collimator of an x-ray imaging system during image acquisition includes receiving rapid scout images at an imaging station. The location of the body regions in one of said images is then automatically detected. The detected location of the body regions is used to generate settings for the collimator. The settings are used for automatically adjusting the collimator to substantially cover the non-body regions and substantially expose the body regions.

30 Claims, 14 Drawing Sheets

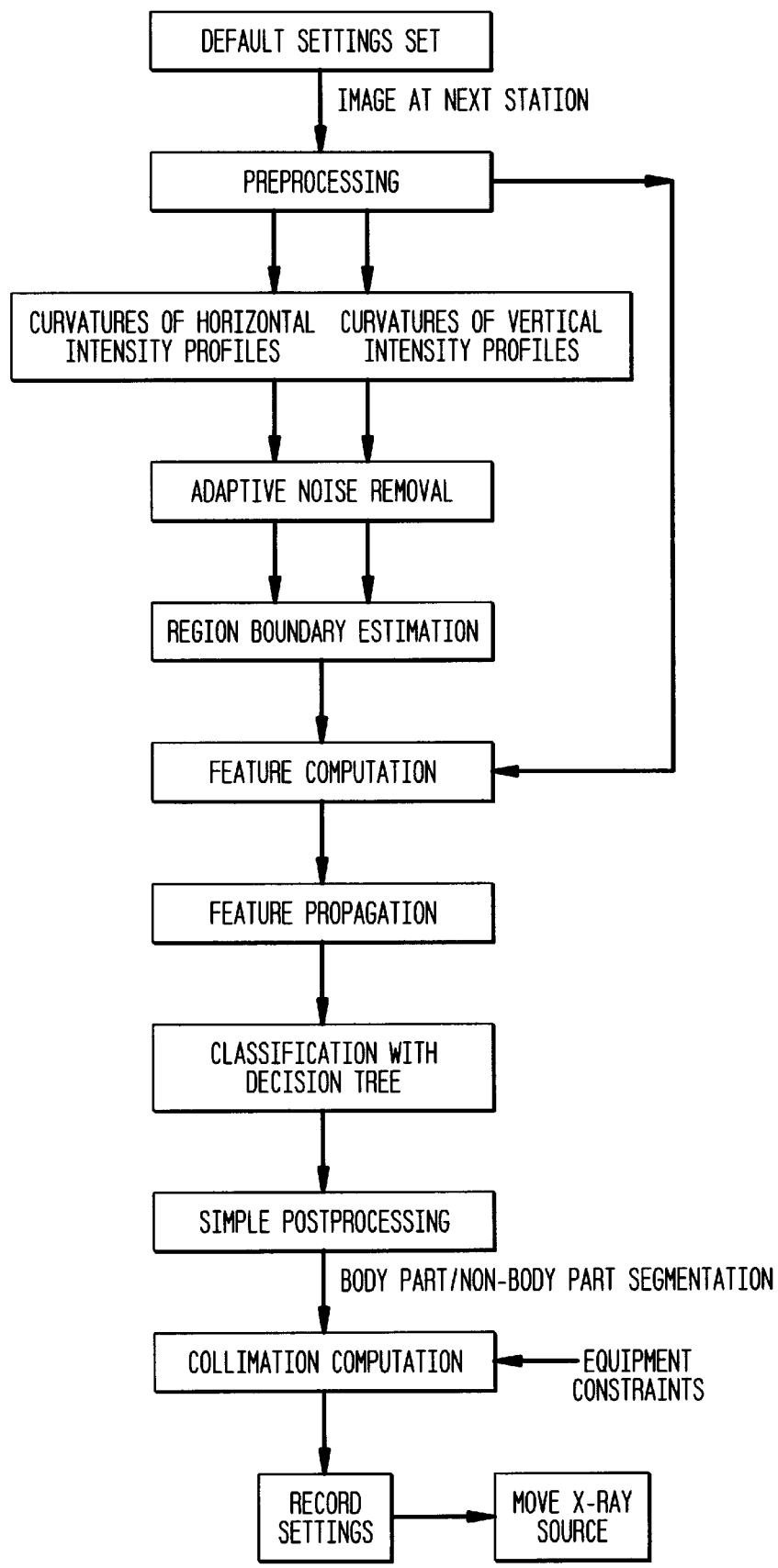

METHOD AND APPARATUS FOR AUTOMATIC COLLIMATION IN X-RAY PERIPHERAL IMAGING

FIELD OF THE INVENTION

This invention relates to x-ray peripheral imaging and in particular, to a method and apparatus for segmenting a peripheral x-ray image into body and non-body part regions at the acquisition time and using that information for automatically setting the collimator of an x-ray imaging system.

BACKGROUND OF THE INVENTION

Radiological procedures, such as x-ray fluoroscopy, are used for diagnosing and treating many diseases. These radiological procedures are generally performed with computerized x-ray imaging systems. Most x-ray imaging systems typically include an x-ray source, an image intensifier and a recording medium.

A major concern in these procedures involves preventing direct exposure and scattered x-rays from reaching the image intensifier or image recording media of the x-ray imaging system. Direct exposure of x-rays to the image intensifier may damage the device and produce diagnostically useless images. The scattered x-rays are also a health concern for medical personnel who perform the procedures. These concerns are addressed by a collimator which collimates the x-ray beam to an extent minimally necessary for imaging the object of interest. Collimation substantially eliminates scattered radiation and improves the imaging quality of the object of interest.

During the x-ray imaging procedure, the collimator must be adjusted each time an image is taken to optimally cover parts of the image where there is no body part. In a typical x-ray imaging procedure, such as a peripheral angiography of the legs, contrast media is injected into a patient and is followed with the imaging equipment. The imaging equipment follows the contrast media by taking images at multiple stations along the legs. In a typical peripheral study of the legs, there may be as many as 5–7 stations. The collimator must be manually adjusted at each of these stations before the image can be taken. This entails manually setting the collimator at each station before a mask run, saving the settings, and retrieving them from a lookup table during actual image acquisition.

Manually setting the collimator increases the time and dosage of radiation to which the patient and the physician are exposed. Moreover, the physician's skill level and other human factors may result in poor images. Most importantly, while the physician is involved in the important activity of caring for the patient, it is preferable for the physician to have as few tedious distractions as possible.

Automatic collimation is an important application of smart image acquisition, which is a new technology with many potential benefits for diagnostic imaging. Peripheral x-ray imaging studies can benefit greatly from the implementation of automatic collimation methods and techniques.

Accordingly, there is a need for a method and system for providing reliable automatic collimation which is fast enough to implement during image acquisition.

SUMMARY OF THE INVENTION

A method for automatically setting the collimator of an x-ray imaging system at image acquisition time includes receiving rapid scout images at an imaging station. The location of body regions in one of the images is then automatically detected. The detected location of the body regions is used to automatically generate settings for the collimator. The settings are used for automatically adjusting the collimator to substantially cover non-body regions.

In another aspect of the invention, an x-ray imaging system for x-ray peripheral imaging includes an x-ray source, an adjustable collimator, an image intensifier, recording media, and automatic collimation means for automatically adjusting the collimator during image acquisition. The automatic collimation means includes region boundary estimation means for dividing the image into regions based on negative curvature extrema of multi-directional pixel intensity line profiles obtained from the image, feature computation means for determining global features corresponding to each of the regions; classifying means for assigning each of the regions as one of the body and non-body regions using the global features; and means for generating settings for the collimator to cover substantially all non-body regions.

BRIEF DESCRIPTION OF THE DRAWINGS

The advantages, nature and various additional features of the invention will appear more fully upon consideration of the illustrative embodiments now to be described in detail in connection with the accompanying drawings. In the drawings:

FIG. 2 is a flow chart depicting the steps of the automatic collimation method of the present invention;

DETAILED DESCRIPTION OF THE INVENTION

Figure 1:
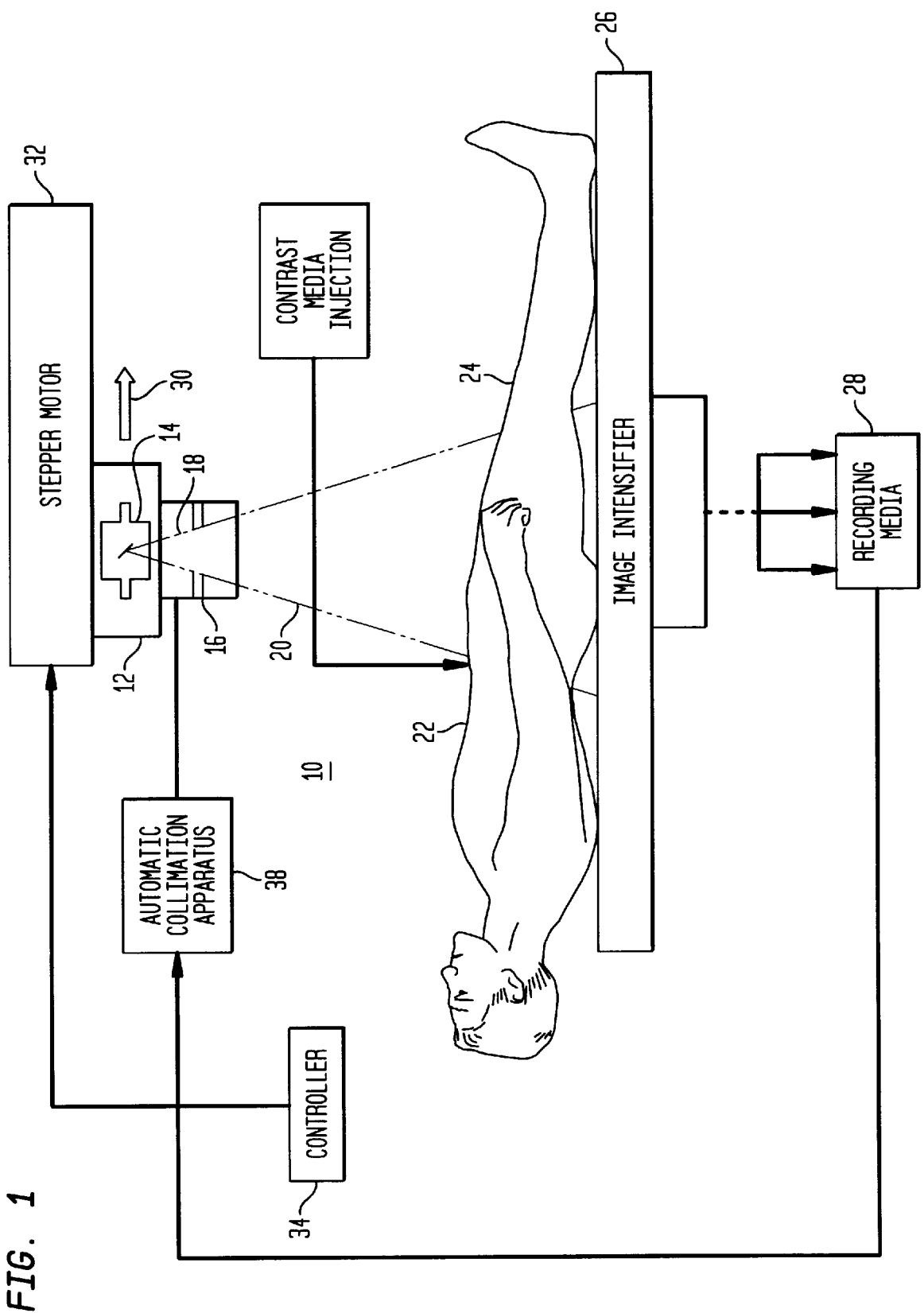
FIG. 1 schematically depicts an embodiment of a computerized x-ray imaging system employing an apparatus for providing automatic collimation according to the present invention.

FIG. 1 schematically depicts one possible embodiment of a computerized x-ray imaging system 10 which employs an apparatus 38 for providing automatic collimation according to the present invention. The x-ray imaging system 10 is used for diagnostic imaging studies of the peripherals (e.g. legs, arms, neck, and head).

The x-ray system 10 comprises a computerized imaging device 12 which includes an x-ray source 14 and a collimator 16. The x-ray source 14 produces an x-ray beam 18 which is collimated by the collimator 16. The collimator 16 may be one of several types of collimators generally used in x-ray studies of the peripherals. For example, the collimator 16 may be a block, a multi-leaf or a finger collimator. The collimated x-ray beam 20 passes through the area of interest 24 of the body 22 and strikes an x-ray image intensifier 26. In other embodiments of the x-ray imaging system, the collimator may be located immediately in front of the image intensifier.

The image intensifier 26 processes the x-ray beam 20 so that it can be recorded by recording media 28 such as film or a CRT. The imaging device 12 is horizontally movable in the direction of arrow 30 so that x-ray images can be taken of the peripherals at a plurality of imaging stations. Leg studies may typically include 5–7 imaging stations. Horizontal movement of the imaging device 12 is provided by a stepper motor 32 which is controlled by a stepper controller 34. A contrast media injection device 36 is provided for injecting a contrast media into the patient 22 just prior to diagnostic imaging. Since x-ray diagnostic imaging is well known and commonly used, the details of these components need not be set forth herein any greater detail.

The automatic collimation apparatus 38 interfaces with the collimator 16 of the system 10. The automatic collimation apparatus 38 performs a method in which an x-ray image of the peripherals is segmented into body parts and non-body parts. The method uses this information to provide the collimator 16 with appropriate collimator settings during image acquisition. The settings are used by the collimator 16 to adjust itself to cover as much of the non-body region and as little of the body region as possible, given the collimator's hardware constraints.

The task of locating the body in an x-ray fluoroscopy image is difficult for a number of reasons. First, segmentation should take place without knowing which part of the body is being looked at. Second, since x-ray fluoroscopy studies use low radiation dosages, the images generally have low signal to noise ratios. Third, soft tissue boundaries often have very poor contrast. Due to the poor contrast makes, conventional edge detection algorithms fail to detect these boundaries. Fourth, existing collimation and noise make local intensity characteristics at a pixel inadequate for determining if it belongs to the body. Finally, segmentation and automatic collimation need to be done at image acquisition time. This places tight constraints on the complexity of image processing operators which can be used.

The method performed by the automatic collimation apparatus 38 of the present invention successfully overcomes these difficulties. When the method is implemented as software, it operates robustly and efficiently on noisy, low contrast, possibly pre-collimated x-ray fluoroscopy images. In comparison with manual segmentation of body parts, the method has very high (>95%) sensitivity and specificity. In one illustrative example of the method efficiently implemented as software, the method runs in less than 500 milliseconds or better per station, on a common 200 MHz Pentium Pro PC running Windows NT 4.0. With the use of parallelism and hardware acceleration, the running time can be further improved.

FIG. 2 is a flow chart depicting the steps of the automatic collimation method of the present invention. The method segments the body regions in an x-ray image of the peripherals from the background (existing collimation, direct exposure). The information about where the body is in an image is used to provide settings for the collimator 16 of the x-ray imaging system 10 shown in FIG. 1.

In step A of the block diagram of FIG. 2, the X-ray source of the x-ray imaging system is adjusted to provide an appropriate low-dosage fluoroscopy, and the collimator is adjusted to predetermined default settings for collimation. This step is repeated at each station.

In step B, one of the incoming images at each station is preprocessed by downsizing and smoothing the image. These preprocessing steps are well known in the art and popularly used, thus further elaboration is not required here.

Step C involves detecting soft-tissue boundaries using directional curvatures of intensity profiles. Finding the soft-tissue boundaries accurately is critical because the subsequent steps of global feature extraction and classification rely on this information. Prior art edge detection methods often fail to detect soft-tissue boundaries in x-ray images because the boundaries often have very low contrast and unusually defined intensity distributions.

Figure 3A:
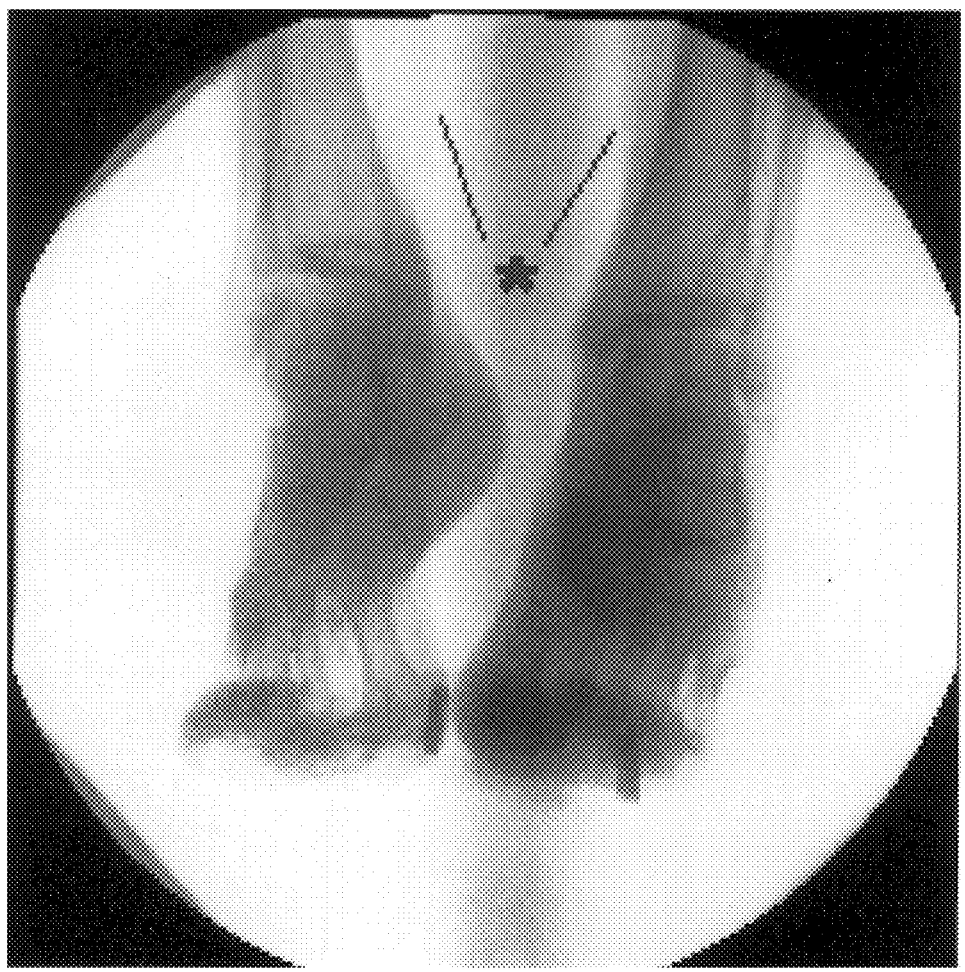
FIG. 3A depicts a peripheral x-ray image with low-contrast soft tissue boundaries near the ankle.
Figure 3B:
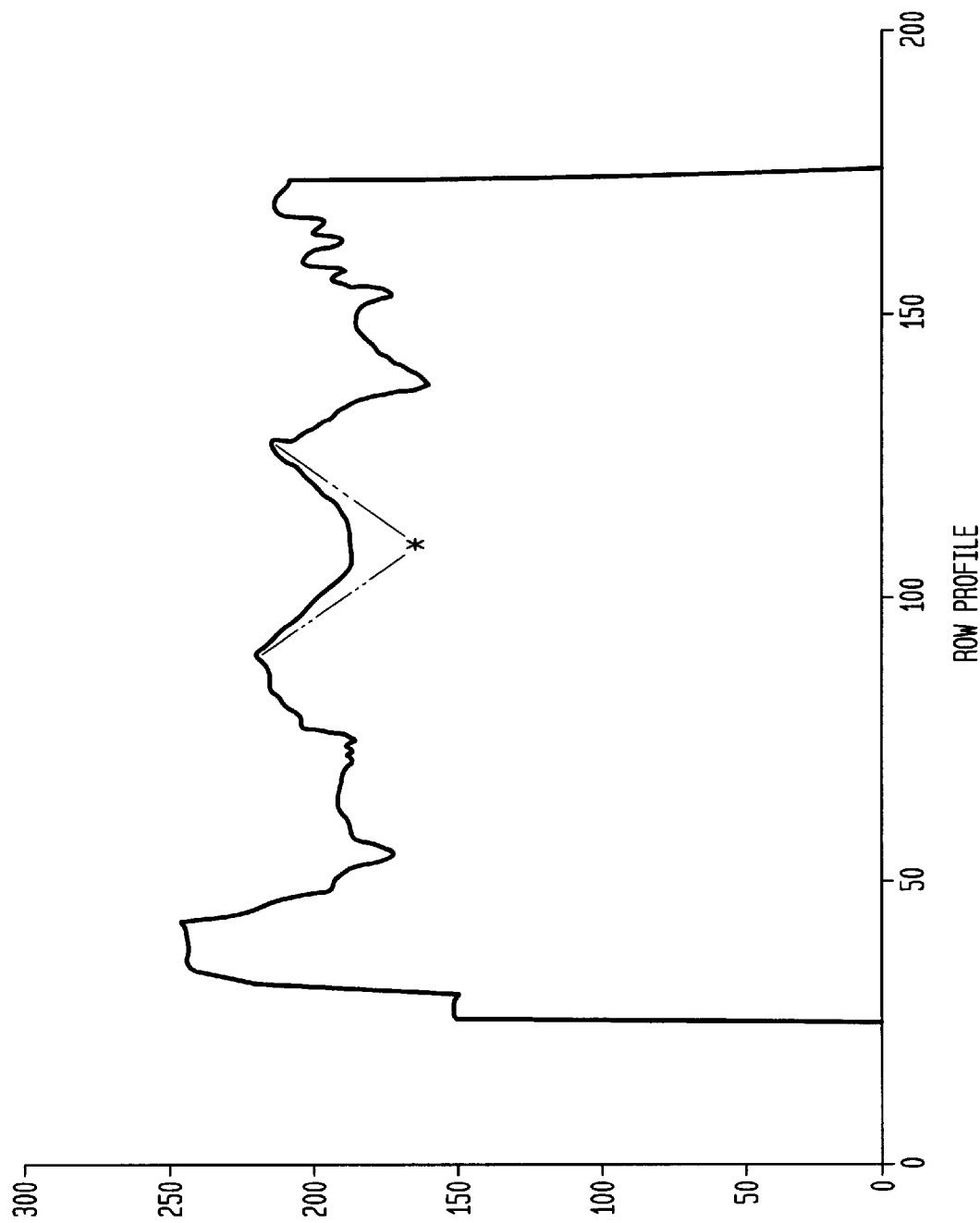
FIG. 3B depicts an intensity profile along a horizontal line passing through the region of interest in FIG. 3A.
Figure 3C:
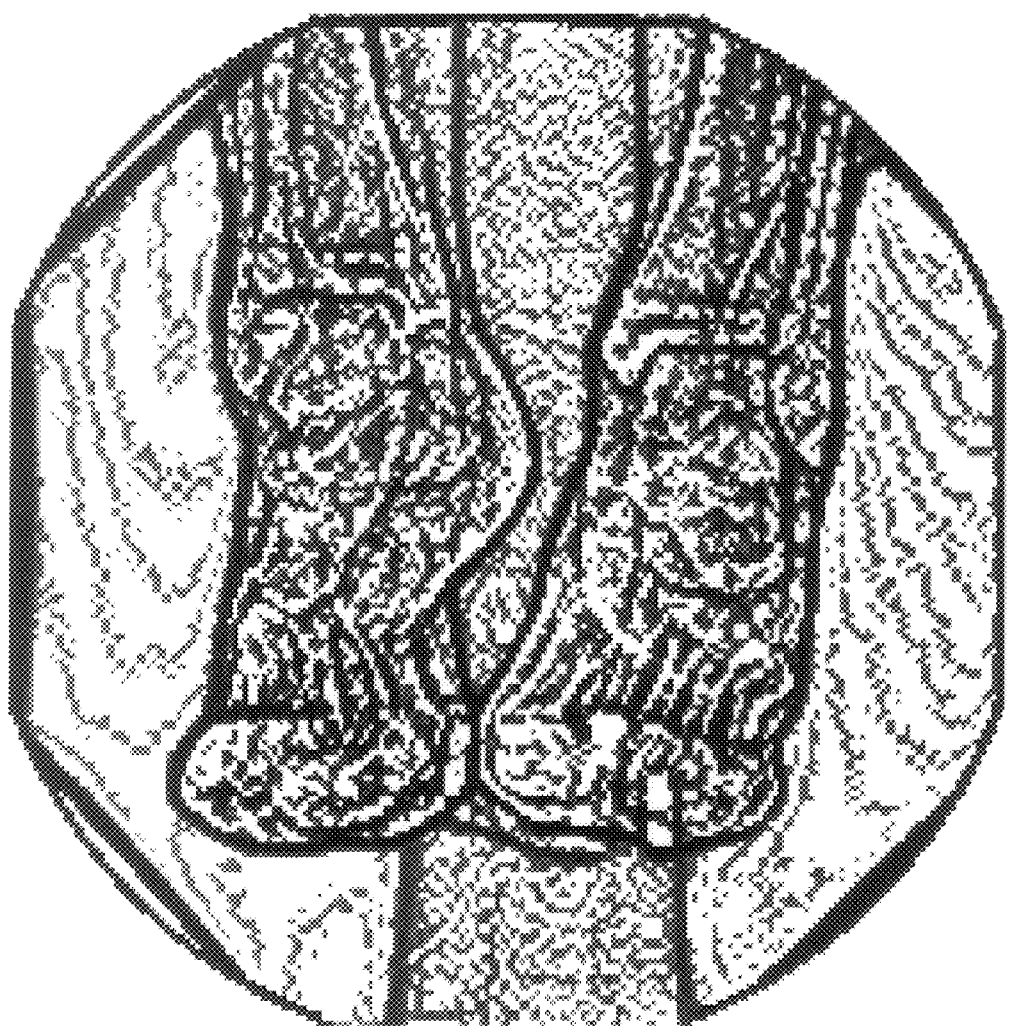
FIG. 3C depicts an image of the line profile curvatures.

Soft-tissue boundaries are detected in the present invention by determining negative curvature points along line profiles of intensity in multiple chosen scanning directions. These provide a reliable indicator of low-contrast boundaries, such as soft-tissue. Even for very low contrast or hazy soft-tissue boundaries, well defined points of negative curvature exist on the line profiles of intensity. This is illustrated in FIG. 3A–3C. FIG. 3A depicts a peripheral x-ray image with low-contrast soft tissue boundaries near the ankle. An intensity profile along a horizontal line passing through the region of interest in FIG. 3A has points of negative curvature corresponding to these soft-tissue boundaries as shown in FIG, 3B. From a histogram equalized image of the line profile curvatures, very low-contrast boundaries are clearly preserved in the negative curvature image of FIG. 3C. Curvatures of line profiles of intensity are computed as follows with the following formulas:

$$Idiff(i,j)=I(i,j)-I(i,j-w))/wdenom(i,j)=w*sqrt(I+Idiff(i,j)^2)$$

$$hcurv(i,j)=(atan(Idiff(ij+w))-atan(Idiff(i,j)))(denom(i,j+w)+(denom(i,j))$$

I(i,j) is defined as the normalized intensity at pixel (i,j), w defines a parameter related to the window width and is dependent on the input image size, and atan is the arc tangent function. The above computation is for horizontal curvatures of line profiles of intensity, however, similar computations can be performed for vertical or other directional curvatures of line profiles of intensity. In the present invention, all positive curvature values are ignored and therefore, removed by zeroing out the positive curvature values. It has been found that soft tissue boundaries are better captured by considering only negative curvatures. The curvature values shown in FIG. 3C are a combination of negative horizontal and vertical curvatures. The combined curvature value at a pixel is the minimum of the horizontal and vertical curvatures.

Although the negative curvature image in FIG. 3C reliably indicates all soft-tissue boundaries, it still contains numerous spurious boundaries. Curvature is a second-order statistic and is therefore, noisy.

Figure 4A:
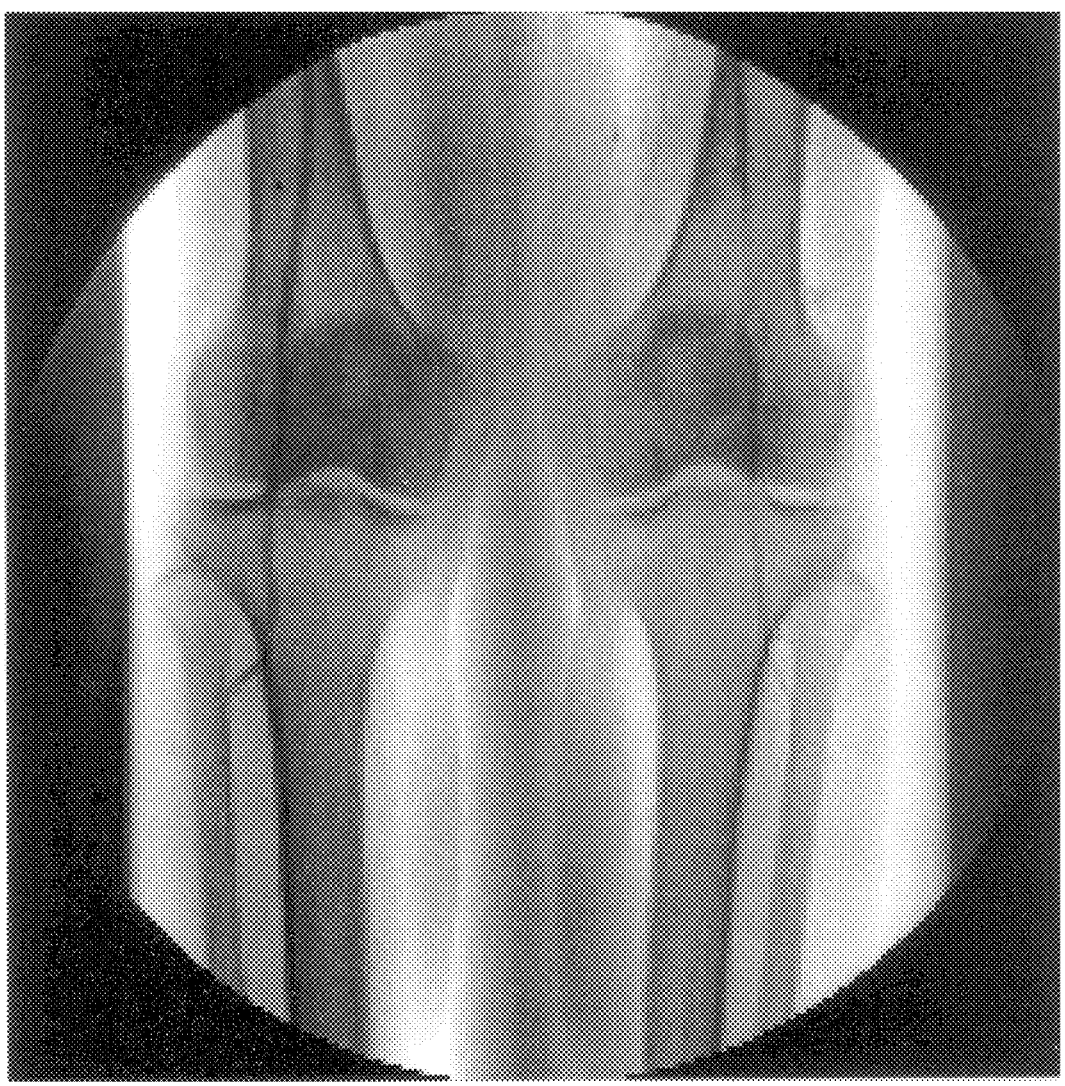
FIG. 4A depicts an intensity image.
Figure 4B:
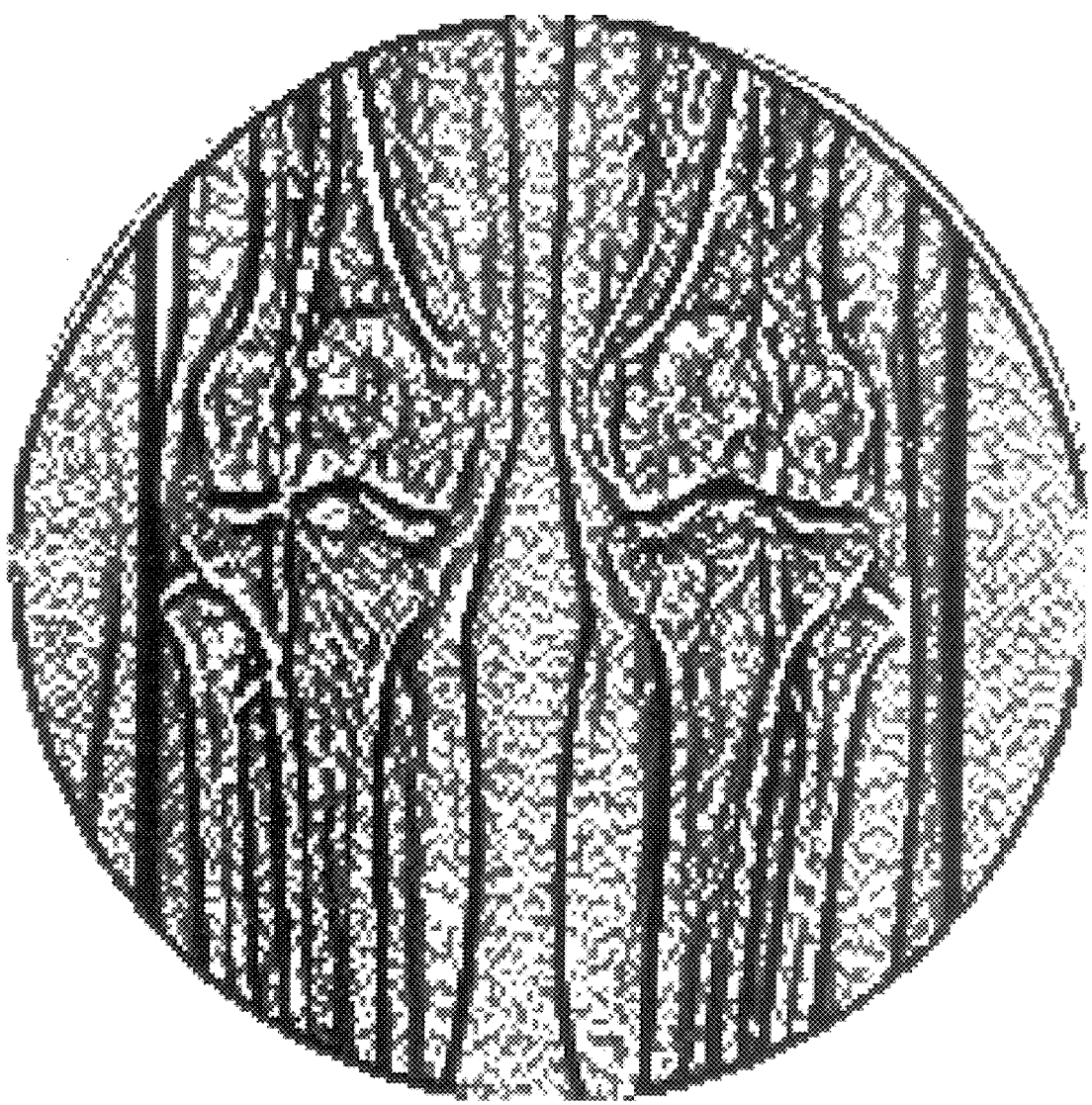
FIG. 4B depicts a noisy line profile negative curvature image corresponding to FIG. 4A.
Figure 4C:
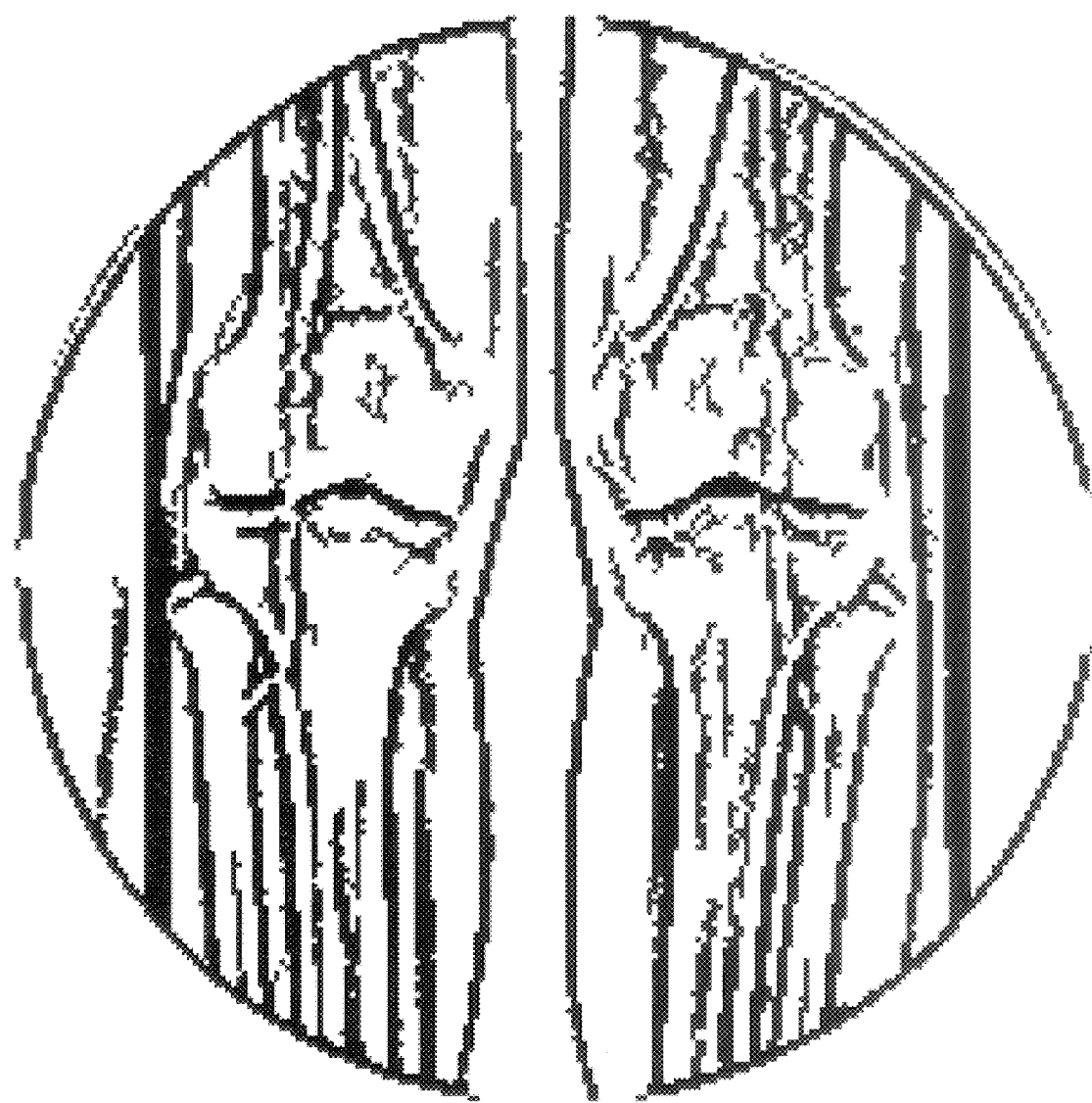
FIG. 4C depicts the negative curvature image of FIG. 4B after adaptively removing the noise.

In order for negative curvatures to be useful, the spurious boundary pixels must be reliably removed while preserving all the important boundaries of the soft-tissues. Accordingly, in step D of the block diagram of FIG. 2, the noise in the negative curvature image is adaptively removed using magnitude and alignment information. Magnitude information alone is not used because it may eliminate very faint soft-tissue boundaries which are desirable to locate. Noise is adaptively removed from the negative curvature image by strengthening well aligned curvature pixels and then finding an adaptive threshold based on the cumulative histogram of curvature values in the image. FIGS. 4A–4C depict adaptive noise removal from negative curvature images. FIG. 4A depicts an intensity image (X-ray image) and FIG. 4B depicts a corresponding noisy line profile negative curvature image. FIG. 4C depicts the negative curvature image of FIG. 4B after adaptively removing the noise. The images of FIGS. 4B and 4C are histogram equalized to show detail.

Figure 5A:
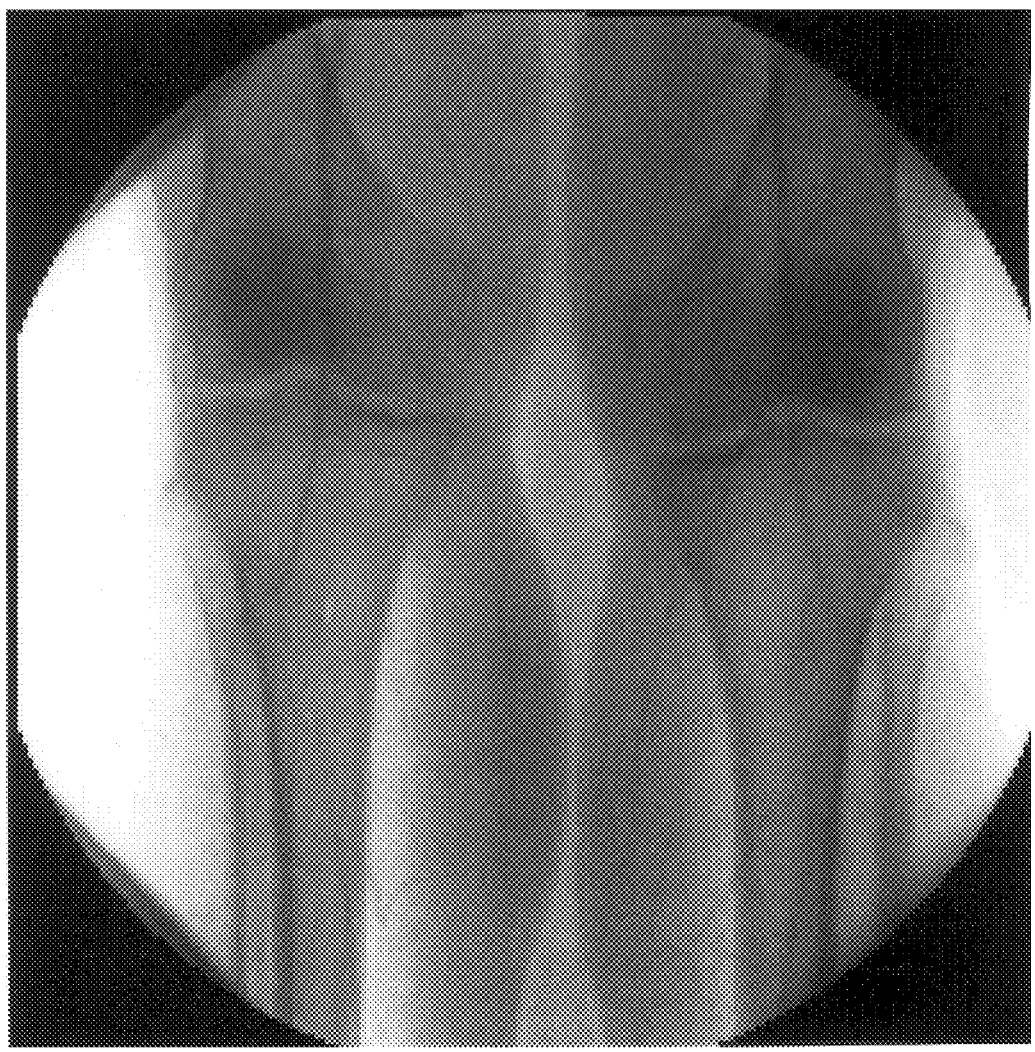
FIG. 5A depicts an intensity image.
Figure 5B:
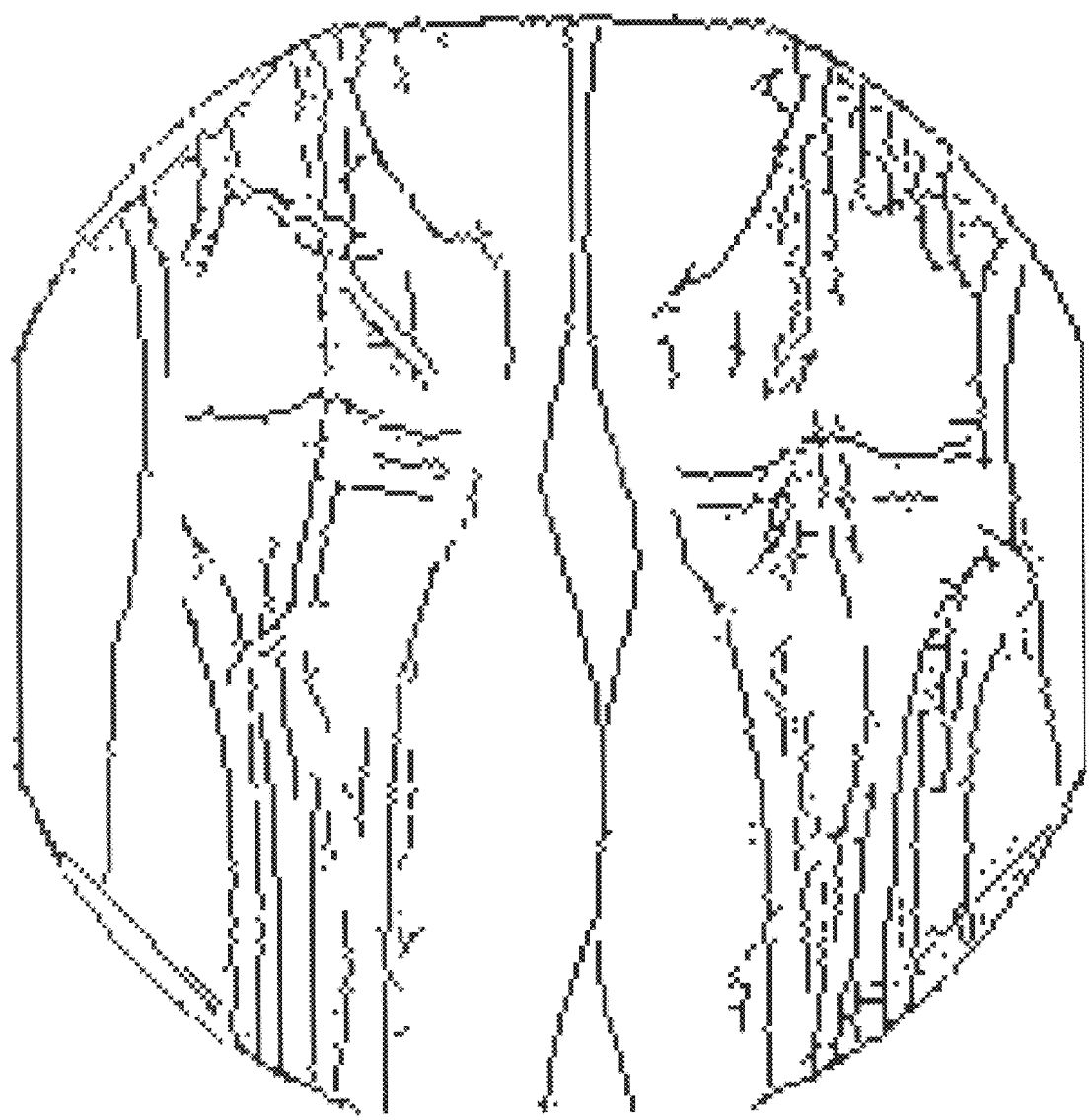
FIG. 5B depicts the region boundaries for the image shown in FIG. 5A.

Step E of the method depicted in FIG. 2 involves dividing the image into "regions". This is accomplished by providing the boundaries of significant regions in the image with a one-pixel representation of the cleaned up negative curvatures. The one-pixel representation is obtained by finding the local extrema in horizontal and vertical directions, combining them and performing simple noise removal using conventional connected components analysis techniques. The region information is for subsequently extracting global feature values which in turn, are used for classification as explained further on in greater detail. FIG. 5B shows the region boundaries for the image shown in FIG. 5A.

In step F of the block diagram of FIG. 2, appropriate features such as range of intensity values, size, etc., are computed along horizontal and vertical lines within each region created in step E. The method of the invention preferably uses three features for segmentation. These features are homogeneity, representative intensity, and station number. Homogeneity is the minimum amount of intensity variation along chosen directions, per pixel, inside a region. Representative intensity is the median intensity in a region. Station number is number of the current station with respect to the full-leg study. Station numbers start at 0 at the pelvic region.

Due to running time constraints, it is necessary that these features be simple. Additional features such as, the size of a region, the location of a region with respect to the station and with respect to the full-leg study, the variance of intensities in the region, etc., have been tried. However, supervised decision tree methods used for classification in the present invention, advantageously indicate which features are the most useful for discrimination. These and traditional feature selection methods have shown that no improvement in the classification results are obtained by adding more features to the above set of three.

Figure 6A:
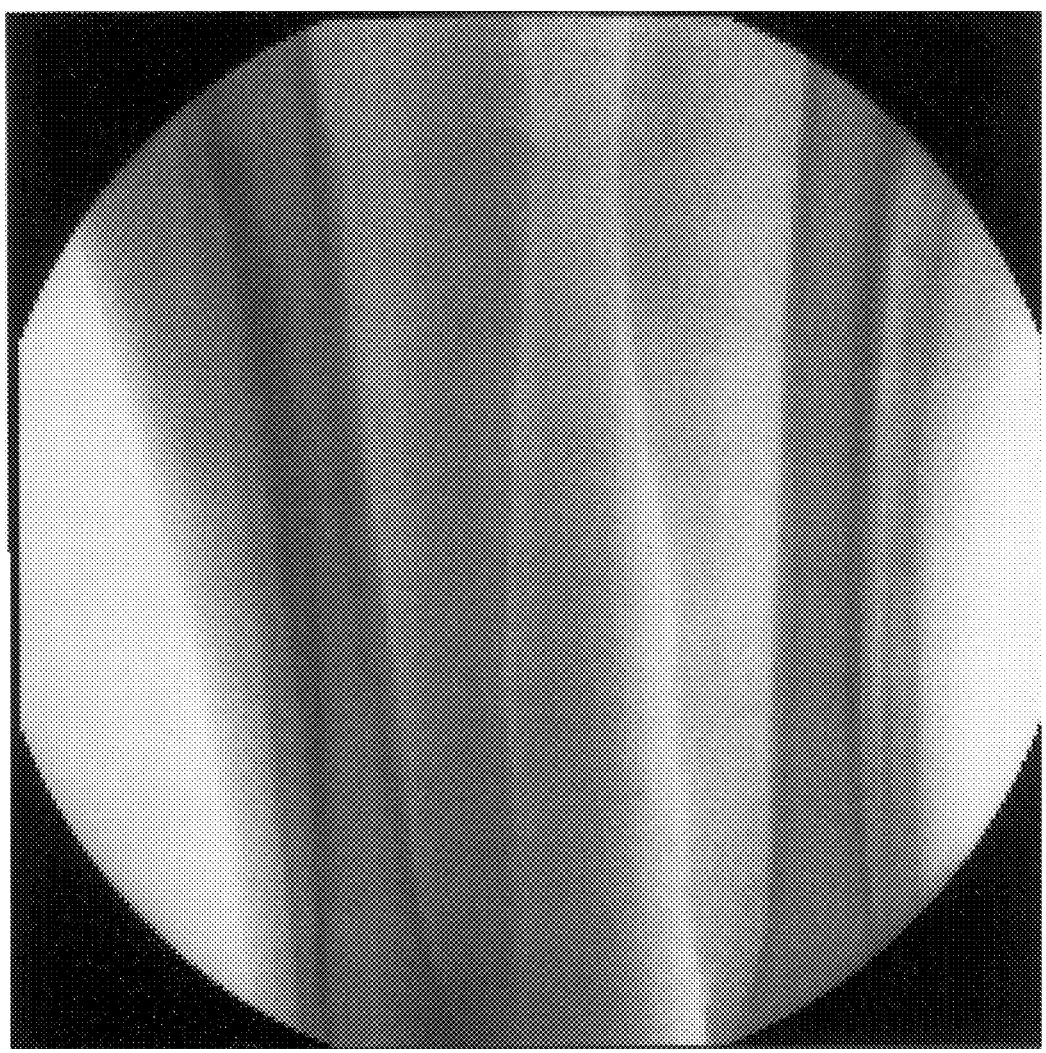
FIGS. 6A–6C depict the homogeneity and representative intensity feature values for a typical image after propagation.
Figure 6B:
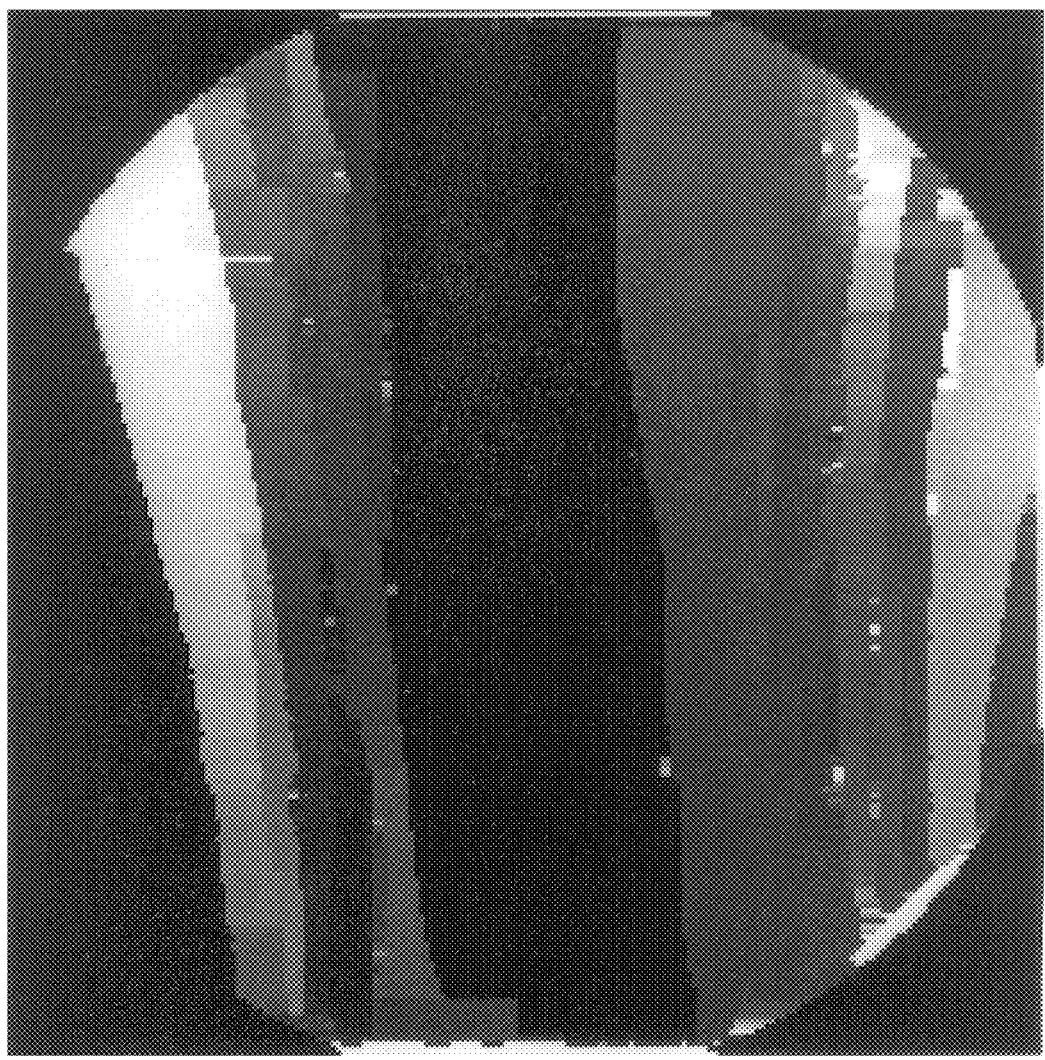
Figure 6C:
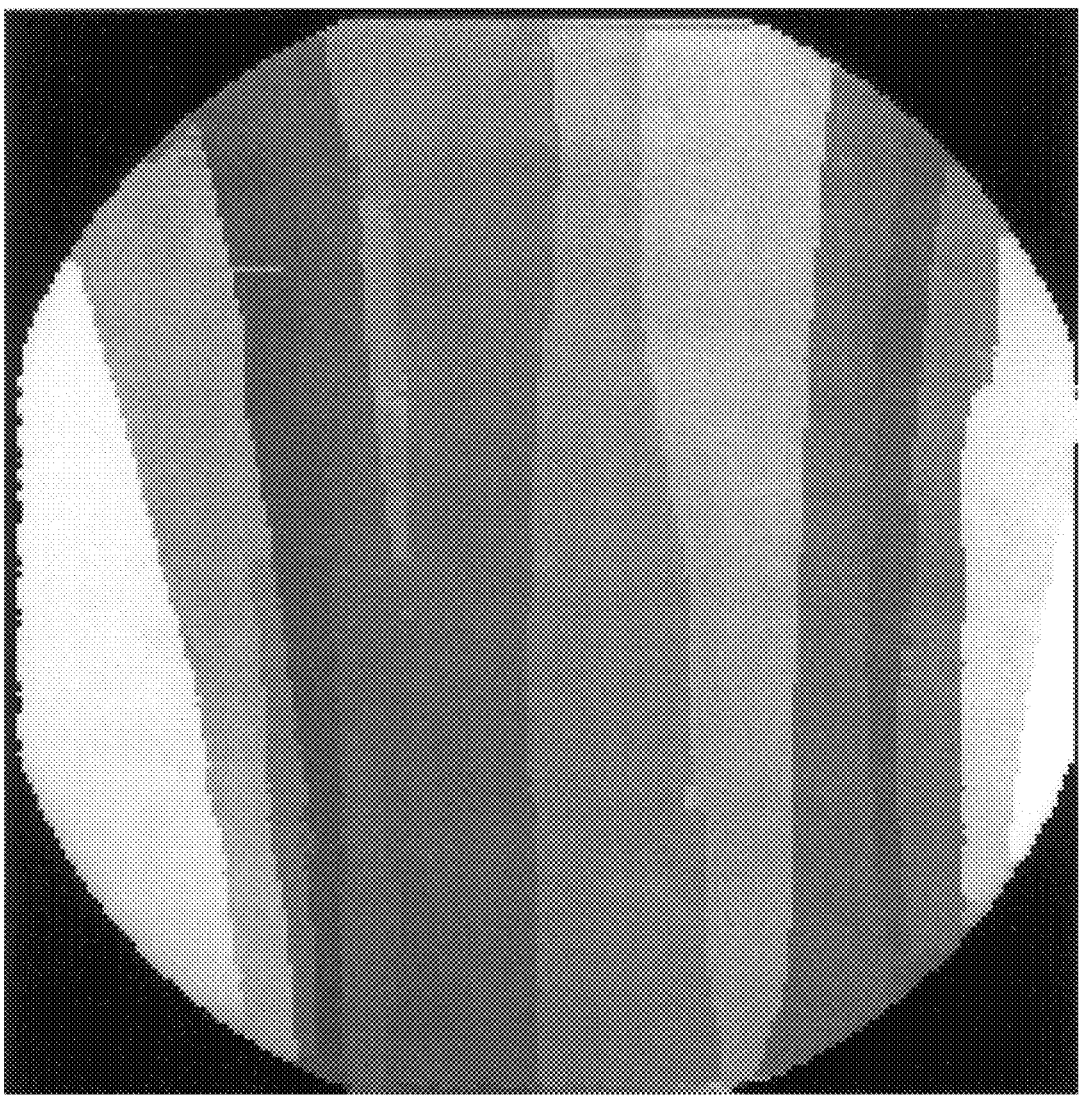

Step G of the method involves inter-region and intra-region propagation of the features. The features are first computed along scan lines in chosen directions in the image and then efficiently propagated over entire regions. Well known adaptive smoothing techniques are used herein for feature value propagation. FIGS. 6A–6C show the homogeneity and representative intensity feature values for a typical image after propagation.

In step H of the block diagram of FIG. 2, each pixel in the image is classified as a body part or a non-body part, based on its feature values, using a decision tree. This involves constructing a set of rules which enable body and non-body regions to be determined on the basis of the feature values. The rules are constructed using supervised learning and are therefore, referred to herein as automatically learned classifiers. Automatically learned classifiers advantageously improve automatically over time, as new data comes in. Binary decision trees are used as the specific classifiers in the present invention. Binary decision trees are easy to understand and analyze and make classification very fast because if/else statements are used. Manually found and hard-coded rules typically used in prior art classification, are not used in the present invention because they may not generalize well, and the rules may need to be reconstructed when new data arrives.

A predetermined number of data points (pixels in the image) are randomly selected as a training set. The training set is then used in a conventional decision tree method or algorithm to automatically construct the binary decision tree. The preferred decision tree method used is a conventional classification and regression tree (CART) method. This method is described by Breiman et al., Classification and Regression Trees, Chapman & Hall Publishers, 1984 (Software available from Salford Systems, Inc.). Since the CART method is well known, it need not be set forth in any great detail herein. However, some of the more important points of this method will now be described.

The CART method takes as input a collection of labeled training instances, each instance having some attributes and a class label and produces a hierarchical decision tree as output. In the present invention, the instances are individual pixels, the attributes are the features computed above and the class labels are body part (1) and non-body part (0). CART then is used to construct binary decision trees from the data. At each stage, CART analyzes the training set to determine the test ("attribute?value→") that best discriminates between the classes, based on a feature evaluation criterion. The training set is then split into two subsets based on the best test. Tree growing continues recursively until no more nodes can be created. Once a full tree is constructed, CART prunes back the tree to remove noise-fitting nodes and/or marginally useful nodes, based on a portion of the training set that is reserved for this purpose.

The preferred binary decision tree used in the present invention is relatively small and has only 160 terminal nodes. Having a small tree is important because it shows that the chosen features are appropriate for the classification task, and that the tree has a high probability of classifying unseen data correctly. If for example, the selected number of data points includes 95,000 data points, a tree with 95,000 terminal nodes can be theoretically built. A 160-node tree, which has high accuracy on hundreds of thousands of unseen data points, indicates that the features used are appropriate for classification.

In using the binary tree for classification, the feature vectors at each pixel are individually "dropped down" the decision tree until a terminal node is reached. The label at the node is then assigned to the pixel.

It should be understood that although the CART method is preferred, other decision tree methods or algorithms may be used if desired.

In step I of the block diagram of FIG. 2, the classification result is post-processed to remove noise. This involves smoothing labels over regions and performing a connected components analysis. Such image processing operators are well known in the art and need no further description.

In step J, a setting for the collimator is automatically determined from the classification result of step I. The collimator setting is selected to cover as much of the non-body part region as is possible while leaving uncovered as much of the body part as is possible. The collimator settings are automatically tailored to the constraints of the particular collimator used, for example, by taking into account the number of leafs, degrees of freedom, etc.

In step k, the imaging system records the automatically computed collimator setting parameters which are subsequently used by the collimator.

In step 1, the x-ray source is moved to the next station and the method is repeated until all the stations are processed and the collimation parameters are recorded by the imaging system.

Figure 7:
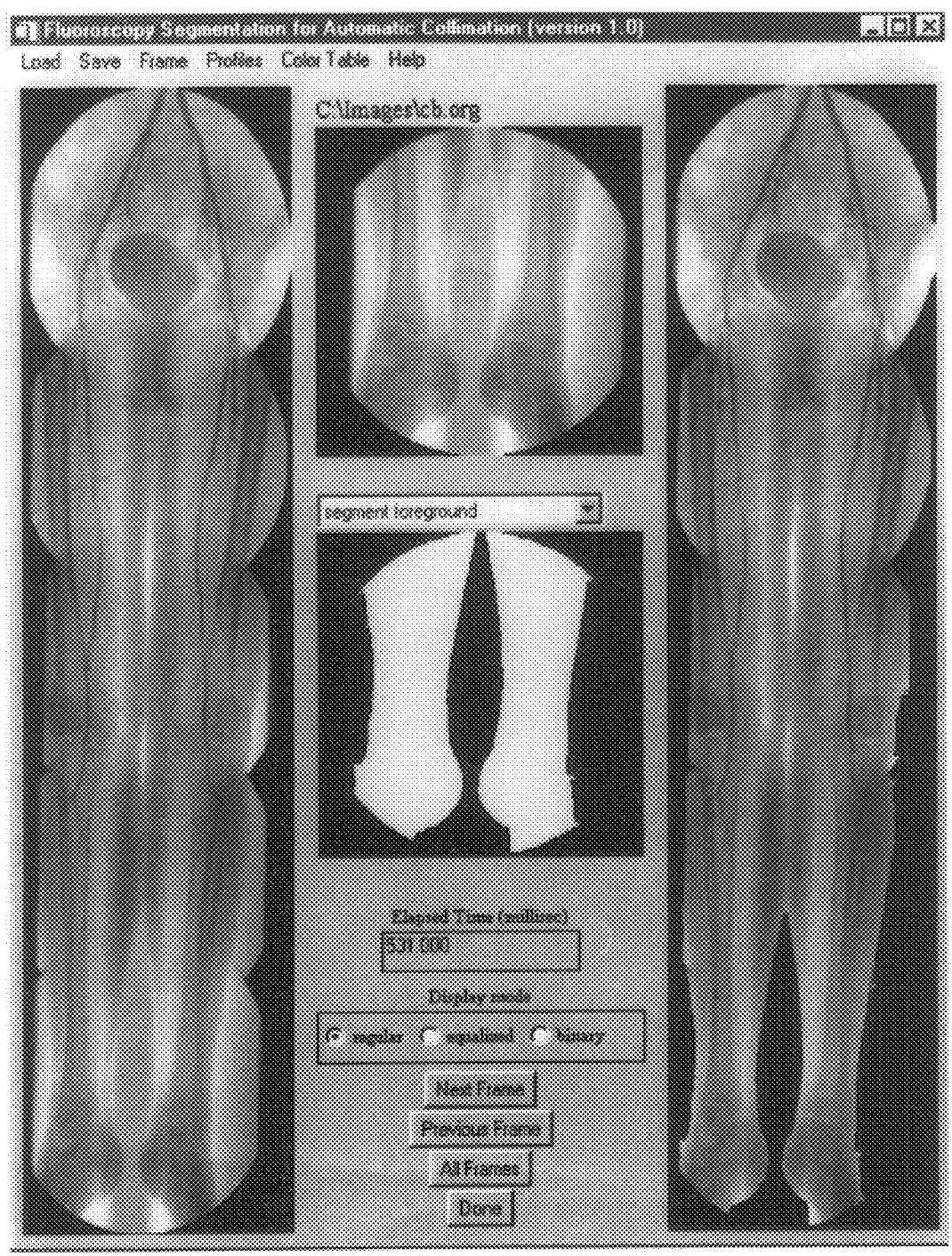
FIG. 7 depicts a graphical user interface which may be displayed by the automatic collimation apparatus.

FIG. 7 depicts a graphical user interface which may be displayed by the automatic collimation apparatus. The images depicted are for a full leg study. It should be noted that other peripheral studies can be used as well. The interface displays multiple station input images 40 for the full leg, the input image of a single station 42, the segmentation result for the one station 44, and results for the full leg 46.

It is understood that the above-described embodiments illustrate only a few of the many possible specific embodiments which can represent applications of the principles of the invention. For example, a human override option may be provided for allowing the physician or operator to override the automatically selected collimator setting if desired. This and other numerous modifications and changes can be made by those skilled in the art without departing from the spirit and scope of the invention.

What is claimed is:

1. A method for automatically setting a collimator of an x-ray imaging system during image acquisition, comprising the steps of:

(a) receiving scout images at an imaging station;

(b) automatically detecting the location of body regions in one of said images by dividing said image into regions based on negative curvature extrema of multi-directional pixel intensity line profiles obtained from said image; and (c) automatically generating settings for said collimator based on the detected location of said body regions, said settings for adjusting said collimator automatically to substantially cover non-body regions.

2. The method according to claim 1, wherein the step of automatically detecting includes the steps of:

determining global features corresponding to each of said regions; and classifying each of said regions as one of said body and non-body regions using said global features.

3. The method according to claim 2, wherein said step of dividing includes the steps of;

obtaining multi-directional pixel intensity line profiles from said image;

detecting negative curvature local extrema from said pixel intensity line profiles;

combining said negative curvature extrema to produce a negative curvature image; and dividing said negative curvature image into a plurality of regions.

4. The method according to claim 3, wherein said step of dividing further includes the step of removing noise from said negative curvature extrema pixels prior to said step of combining.

5. The method according to claim 2, wherein said step of detecting includes the step of removing noise from said negative curvatures of pixel intensity profiles obtained from said image.

6. The method according to claim 5, wherein said step of removing noise includes the steps of:

intensifying well aligned curvature pixels in said negative curvatures of pixel intensity line profiles;

determining an adaptive threshold value to identify pixels which represent noise in said negative curvatures of pixel intensity line profiles; and removing pixels from said negative curvatures of pixel intensity line profiles which have been identified as noise.

7. The method according to claim 2, wherein said features include minimum intensity variations per pixel along chosen directions inside each of said regions, median intensity in each of said regions, and the serial number of said imaging station.

8. The method according to claim 2, wherein said step of determining includes the steps of:

determining features along lines in chosen directions;

propagating features within each of said regions; and propagating features across said regions.

9. The method according to claim 2, wherein said step of classifying includes the steps of:

providing a hierarchical decision tree constructed from a collection of training pixels, each of said pixels having said features and labeled as one of said body region and said non-body region; and classifying each pixel according to said feature values, as one of said body regions and said non-body regions using said decision tree.

10. The method according to claim 2, wherein said step of classifying includes the step of removing noise from said classified regions prior to said step of generating.

11. The method according to claim 1, wherein said imaging station is one of a plurality of imaging stations and further comprising the steps of:

receiving scout images at all of said imaging stations and repeat steps (b)–(c) for a selected one of said images at each of said imaging stations;

saving said settings obtained at said stations; and adjusting said collimator at each of said stations according to said corresponding saved setting during the diagnostic image acquisition.

12. A method for automatically segmenting an x-ray image into body regions and non-body regions, comprising the steps of:

(a) receiving scout images at an imaging station;

(b) dividing one of said images into regions based on negative curvature extrema of multi-directional pixel intensity line profiles obtained from said one image, (c) determining global features corresponding to each of said regions; and (d) classifying each of said regions as one of a body region and non-body region using said global features.

13. The method according to claim 12, wherein said step of dividing includes the steps of;

obtaining multi-directional pixel intensity line profiles from said image;

detecting negative curvature local extrema from said pixel intensity line profiles;

combining said negative curvature extrema to produce a negative curvature image; and dividing said negative curvature image into a plurality of regions.

14. The method according to claim 13, wherein said step of dividing further includes the step of removing noise from said negative curvature extrema pixels prior to said step of combining.

15. The method according to claim 13, wherein said step of determining includes the step of removing noise from said negative curvatures of pixel intensity profiles obtained from said image.

16. The method according to claim 15, wherein said step of removing noise includes the steps of:

intensifying aligned curvature pixels in said negative curvatures of pixel intensity line profiles;

determining an adaptive threshold value to identify pixels which represent noise in said negative curvatures of pixel intensity line profiles; and removing pixels from said negative curvatures of pixel intensity line profiles which have been identified as noise.

17. The method according to claim 12, wherein said features include minimum intensity variations per pixel along chosen directions inside each of said regions, median intensity in each of said regions, and the serial number of said imaging station.

18. The method according to claim 12, wherein said step of determining includes the steps of:

determining features along lines in chosen directions;

propagating features within each of said regions; and propagating features across said regions.

19. The method according to claim 12, wherein said step of classifying includes the steps of:

providing a hierarchical decision tree constructed from a collection of training pixels, each of said pixels having said features and labeled as one of said body region and said non-body region; and classifying each of said pixels according to said features, as one of said body regions and said non-body regions using said decision tree.

20. The method according to claim 12, wherein said step of classifying includes the step of removing noise from said classified regions prior to said step of generating.

21. An x-ray imaging system used for x-ray peripheral imaging, comprising:

an x-ray source for producing x-ray radiation;

an adjustable collimator for substantially preventing x-ray radiation exposure of non-body regions while substantially allowing x-ray radiation exposure of body regions;

an image intensifier for receiving the x-ray radiation after it passes through an area of interest and converting the received x-ray radiation into an x-ray image which can be recorded;

recording media for recording said x-ray image; and automatic collimation means for automatically adjusting said collimator during image acquisition, said automatic collimation means including:

region boundary estimation means for dividing said image into regions based on negative curvature extrema of multi-directional pixel intensity line profiles obtained from said image;

feature computation means for determining global features corresponding to each of said regions;

classifying means for assigning each of said regions as one of said body and non-body regions using said global features; and means for generating settings for said collimator based on said classification to substantially cover said non-body regions.

22. The system according to claim 21, wherein said region boundary estimation means includes means for obtaining multi-directional pixel intensity line profiles from said image;

means for detecting negative curvature local extrema from said pixel intensity line profiles;

means for combining said negative curvature pixel extrema to produce a negative curvature image; and means for dividing said negative curvature image into a plurality of regions.

23. The system according to claim 22, wherein said region boundary estimation means further includes means for removing noise from said negative curvature local extrema pixels prior to combining said negative curvature local extrema.

24. The system according to claim 22, wherein said negative curvature local extrema detection means includes means for removing noise from said negative curvatures of pixel intensity profiles obtained from said image.

25. The system according to claim 24, wherein said noise removing means intensifies well aligned curvature pixels in said negative curvature of pixel intensity line profile, determines an adaptive threshold value to identify pixels which represent noise in said negative curvatures of pixel intensity line profiles, and removes pixels from said negative curvatures of pixel intensity line profiles which have been identified as noise.

26. The system according to claim 21, wherein said features include minimum intensity variations per pixel along chosen directions inside each of said regions, median intensity in each of said regions, and the serial number of said imaging station.

27. The system according to claim 21, wherein said feature computation means includes means for determining features along lines in chosen directions, means for propagating features within each of said regions, and means for propagating features across said regions.

28. The system according to claim 21, wherein said classification means includes:

means for constructing a hierarchical decision tree from a collection of training pixels, each of said pixels having said features and labeled as one of said body region and said non-body region; and means for classifying said pixels according to its feature values, as one of said body regions and said non-body regions using said decision tree.

29. The system according to claim 21, wherein said automatic collimation means further comprises means for removing noise from said classified regions.

30. The system according to claim 21, wherein said means for generating settings takes into account the constraints of the collimator in generating said settings.

* * * * *